(12) United States Patent
Lee et al.

(10) Patent No.: US 10,611,737 B1
(45) Date of Patent: Apr. 7, 2020

(54) METHOD FOR PREPARING ARYL 2-TETRAZOL-2-YL KETONE WITH IMPROVED SELECTIVITY

(71) Applicant: SK BIOPHARMACEUTICALS CO., LTD., Gyeonggi-do (KR)

(72) Inventors: Kyuwoong Lee, Gyeonggi-do (KR); Kyungmi Cha, Gyeonggi-do (KR); Suyeon Yeom, Gyeonggi-do (KR); Jiseon Woo, Gyeonggi-do (KR)

(73) Assignee: SK BIOPHARMACEUTICALS CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/662,547

(22) Filed: Oct. 24, 2019

(51) Int. Cl.
*C07D 257/04* (2006.01)

(52) U.S. Cl.
CPC .................. *C07D 257/04* (2013.01)

(58) Field of Classification Search
CPC ..................................... C07D 257/04
See application file for complete search history.

(56) References Cited

U.S. PATENT DOCUMENTS 7,598,279 B2   10/2009   Choi et al.

FOREIGN PATENT DOCUMENTS

WO    WO-2011/046380 A2    4/2011

OTHER PUBLICATIONS

Moderhack, D. and Lembcke, A. (1986) "Synthesis and Properties of Tetrazolium N-Phenacylides. "*Journal of the Chemical Society, Perkin Transactions 1: Organic and Bio-Organic Chemistry* (1972-1999), 7:1157-1163.

Aoyama, T. and Shioiri, T. (1982) "New methods and reagents in organic synthesis, 31, 1) lithium trimethylsilyldiazomethane: A new synthon for the preparation of tetrazoles." *Chem. Pharm. Bull.*, 30(9):3450-3452.

*Primary Examiner* — Laura L Stockton

(74) *Attorney, Agent, or Firm* — Harness, Dickey & Pierce, P.L.C.

(57) ABSTRACT

The present disclosure relates to a method for preparing aryl 2-tetrazol-2-yl ketone of the following Formula 1a with improved selectivity:

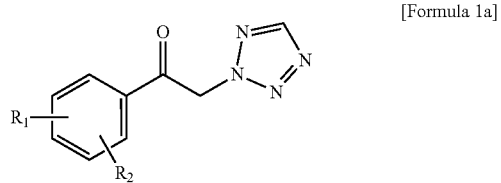

[Formula 1a]

wherein $R_1$ and $R_2$ are the same as defined herein.

12 Claims, 2 Drawing Sheets

METHOD FOR PREPARING ARYL 2-TETRAZOL-2-YL KETONE WITH IMPROVED SELECTIVITY

FIELD

The present disclosure relates to a method for preparing aryl 2-tetrazol-2-yl ketone of Formula 1a with improved selectivity.

[Formula 1a]

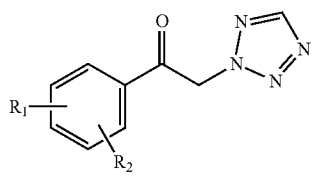

wherein $R_1$ and $R_2$ are as defined herein.

BACKGROUND

Carbamic acid (R)-1-aryl-2-tetrazolyl-ethyl ester (hereinafter also referred to as "carbamate compound") is useful in the treatment of CNS disorders, particularly anxiety, depression, convulsions, epilepsy, migraine, manic depression, drug abuse, smoking, attention deficit hyperactivity disorder (ADHD), obesity, sleep disorders, neuropathic pain, stroke, cognitive impairment, neurodegeneration, muscle spasm due to stroke and the like, according to its anticonvulsant effects.

The carbamate compound is prepared from a compound of Formula 1a, which is obtained from a substitution reaction of a compound of Formula 2 and a compound of Formula 3, as an intermediate. Conventionally, a base is added to the compound of Formula 2, and a tetrazole solution is then added thereto to carry out a substitution reaction. However, in this case, the compound of Formula 1b, which is a positional isomer thereof, in addition to the desired compound of Formula 1a, is obtained together as a mixture by the substitution reaction (WO 2011/046380).

[Formula 2]

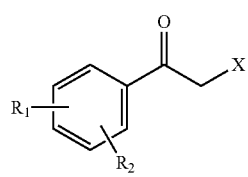

[Formula 3]

[Formula 1a]

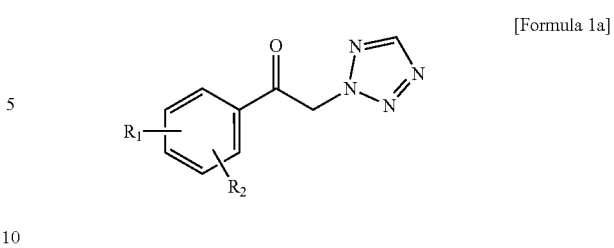

[Formula 1b]

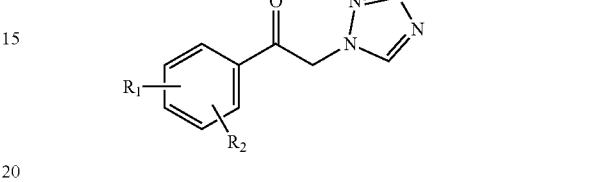

(In the Formulas, $R_1$ and $R_2$ are each independently selected from the group consisting of hydrogen, halogen, perfluoroalkyl having 1 to 8 carbon atoms, alkyl having 1 to 8 carbon atoms, thioalkoxy having 1 to 8 carbon atoms and alkoxy having 1 to 8 carbon atoms; and X is a leaving group)

Furthermore, when the compound of Formula 2 and the compound of Formula 3 are subjected to the substitution reaction, the reaction selectivity of number 1 nitrogen of the compound of Formula 3 is better than the reaction selectivity of number 2 nitrogen, and thus the compound of Formula 1b is produced with superior selectivity with respect to the compound of Formula 1a (Journal of the Chemical Society, Perkin Transactions 1: Organic and Bio-Organic Chemistry (1972-1999), (7), 1157-63; 1986). Therefore, according to the conventional method, the compound of Formula 1a used for preparing the carbamate compound is less produced than the compound of Formula 1b, and thus the yield is low when preparing the carbamate compound by using the compound of Formula 2 and the compound of Formula 3 as starting materials.

In this regard, there is an alternative method for selectively preparing only a compound of the same form as substituted with number 2 nitrogen by synthesizing a tetrazole ring shape (Chem. Pharm. Bull. 30(9) 3450-3452; 1982). However, there may be problems in that it is difficult to be commercially used since a diazomethane-based material—which has a risk of explosion during the reaction—is used, and 2 equivalents or more of lithium diisopropylamide is used as a raw material.

As such, there is a need for developing a method that the aryl 2-tetrazol-2-yl ketone of Formula 1a may be prepared from the compound of Formula 2 and the compound of Formula 3 with better selectivity than the aryl 2-tetrazol-1-yl ketone of Formula 1b, and as a result, can be commercialized while obtaining the aryl 2-tetrazol-2-yl ketone of Formula 1a and the carbamate compound in high yield.

SUMMARY

Technical Problem

The purpose of the present disclosure is to provide a commercially available method capable of improving the productivity of a carbamate compound by more selectively synthesizing aryl 2-tetrazol-2-yl ketone, which is useful as an intermediate of carbamate compound, in large scale.

Solution to Problem

One aspect of the present disclosure provides a method for preparing a compound of Formula 1a, which comprises a step of reacting a compound of Formula 2 with a salt of a compound of Formula 3:

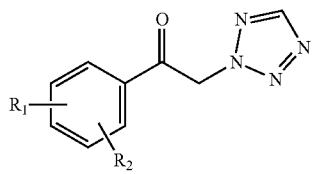

[Formula 1a]

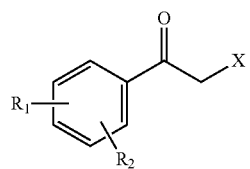

[Formula 2]

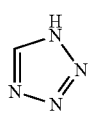

[Formula 3]

wherein $R_1$ and $R_2$ are each independently selected from the group consisting of hydrogen, halogen, perfluoroalkyl having 1 to 8 carbon atoms, alkyl having 1 to 8 carbon atoms, thioalkoxy having 1 to 8 carbon atoms, and alkoxy having 1 to 8 carbon atoms; and X is a leaving group.

Another aspect of the present disclosure provides a method for increasing the selectivity of a compound of Formula 1a by using a salt of a compound of Formula 3 in the synthesis of a compound of Formula 1a and a compound of Formula 1b from a compound of Formula 2 and a compound of Formula 3:

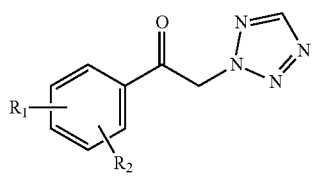

[Formula 1a]

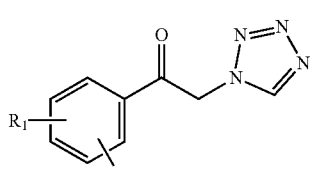

[Formula 1b]

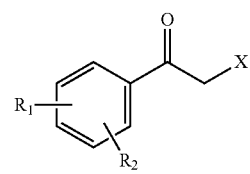

[Formula 2]

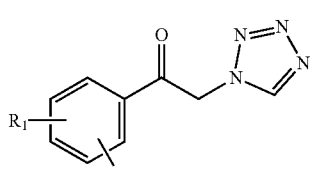

[Formula 3]

wherein $R_1$, $R_2$ and X are the same as defined above.

Another aspect of the present disclosure provides a method of preparing a compound of Formula 4, comprising: (1) reacting a compound of Formula 2 with a salt of a compound of Formula 3; (2) separating the compound of Formula 1a from a mixture obtained by the reaction of step (1); and (3) reducing the compound of Formula 1a separated in step (2) and carbamating the reduced compound of Formula 1a:

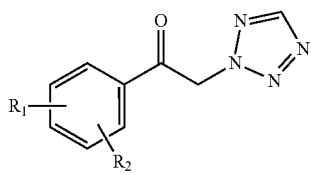

[Formula 1a]

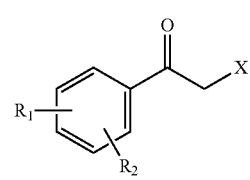

[Formula 2]

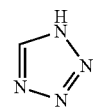

[Formula 3]

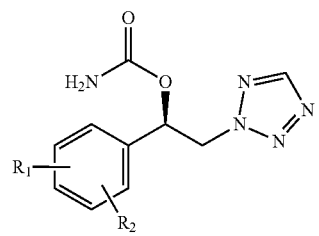

[Formula 4]

wherein $R_1$, $R_2$ and X are the same as defined above.

Another aspect of the present disclosure provides a method for separating a compound of Formula 1a from a mixture comprising a compound of Formula 1a and a compound of 1b by heat treating the mixture comprising the compound of chemical formula 1a and the compound of Formula 1b to produce a compound of Formula 5 and removing this compound:

[Formula 1a]

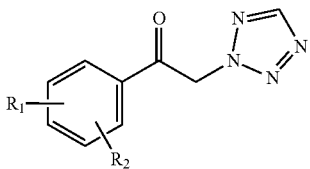

[Formula 1b]

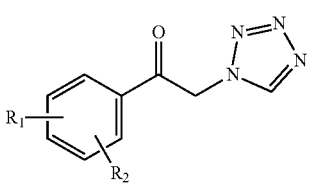

[Formula 5]

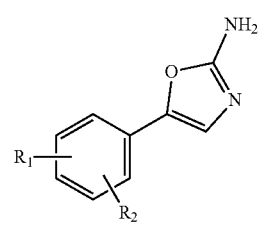

wherein $R_1$ and $R_2$ are the same as defined above.

Another aspect of the present disclosure provides a method for preparing a compound of Formula 1a, comprising: reacting a compound of Formula 2 with a salt of a compound of Formula 3; and purifying the reaction product of the salt of the compound of Formula 3 and the compound of Formula 2, wherein the purifying step comprises a crystallizing process or a heat treatment process:

[Formula 1a]

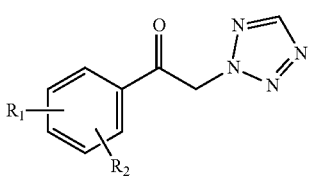

[Formula 2]

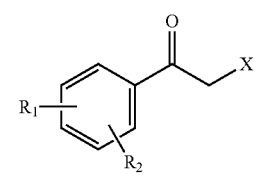

[Formula 3]

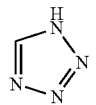

wherein $R_1$, $R_2$ and X are the same as defined above.

Effects of the Invention

According to the present disclosure, the productivity of carbamate compounds can be improved remarkably as a result by more selectively synthesizing aryl 2-tetrazol-2-yl ketone, in large scale, which is useful as an intermediate of carbamate compound, through a simple process.

DETAILED DESCRIPTION

Figure 1:
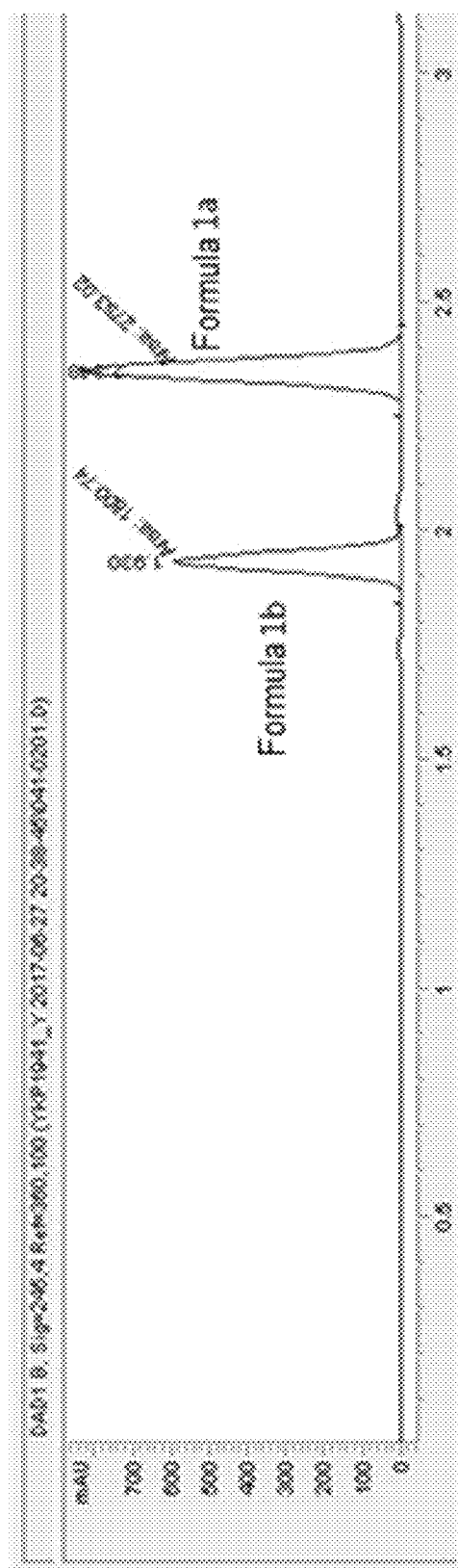
FIG. 1 shows HPLC results of the ratio for the mixture of the compound of Formula 1a and the compound of Formula 1b in the reaction mixture produced in Example 1.

Hereinafter, the present disclosure is described in detail.

A method for preparing a compound of Formula 1a according to one aspect of the present disclosure comprises a step of reacting a compound of Formula 2 with a salt of a compound of Formula 3:

[Formula 1a]

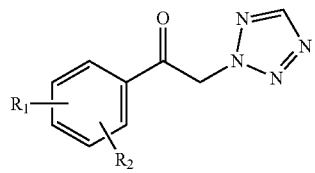

[Formula 2]

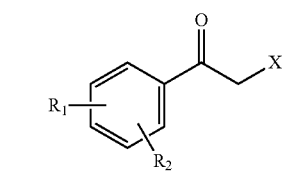

[Formula 3]

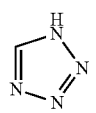

wherein $R_1$ and $R_2$ are each independently selected from the group consisting of hydrogen, halogen, perfluoroalkyl having 1 to 8 carbon atoms, alkyl having 1 to 8 carbon atoms, thioalkoxy having 1 to 8 carbon atoms, and alkoxy having 1 to 8 carbon atoms, and more specifically selected from the group consisting of hydrogen, halogen, perfluoroalkyl having 1 to 4 carbon atoms, alkyl having 1 to 4 carbon atoms, and alkoxy having 1 to 4 carbon atoms; and X is a leaving group, and more specifically selected from halides such as chloride, bromide and the like, and sulfonates such as mesylate, tosylate, 4-nitrophenyl sulfonate and the like.

The salt of the compound of Formula 3 is obtained by reacting the compound of Formula 3 with a base, and the salt may be an inorganic salt or an organic salt.

In one embodiment, the inorganic salt of the compound of Formula 3 may be a metal salt, more specifically an alkali metal salt, and even more specifically a lithium salt, a sodium salt, a potassium salt or a cesium salt.

In one embodiment, the inorganic salt of the compound of Formula 3 may be obtained by reacting the compound of Formula 3 with an inorganic base. The inorganic base may be a metal hydroxide (e.g., lithium hydroxide, sodium hydroxide, potassium hydroxide, etc.) or a metal carbonate (e.g., lithium carbonate, sodium carbonate, potassium carbonate, cesium carbonate, etc.), but is not limited thereto.

In one embodiment, the organic salt of the compound of Formula 3 may be obtained by reacting the compound of Formula 3 with an organic base. The organic base may be an amine compound (e.g., triethylamine, diisopropylethylamine, etc.), but is not limited thereto.

The reaction between the compound of Formula 3 and the base may be carried out at room temperature, and the reaction solvent may be water, acetonitrile, tetrahydrofuran, 2-methyltetrahydrofuran, ethyl acetate, isopropyl acetate, n-butyl acetate, dichloromethane, chloroform, 1,4-dioxane, $C_1$-$C_4$ lower alcohol (e.g., methanol, ethanol, propanol, butanol), alone or in combination thereof.

According to one embodiment, the compound of Formula 3 and the base are reacted in a reaction solvent, and then the salt of the compound of Formula 3 separated from the reaction product may be reacted with the compound of Formula 2.

According to another embodiment, after reacting the compound of Formula 3 with the base, the compound of Formula 2 may be added to the reaction product to react with the salt of the compound of Formula 3.

The reaction between the salt of the compound of Formula 3 and the compound of Formula 2 may be carried out at room temperature, and the reaction solvent may be water, acetonitrile, tetrahydrofuran, 2-methyltetrahydrofuran, ethyl acetate, isopropyl acetate, n-butyl acetate, dichloromethane, chloroform, 1,4-dioxane, $C_1$-$C_4$ lower alcohol (e.g., methanol, ethanol, propanol, butanol), alone or in combination thereof.

The reaction product of the salt of the compound of Formula 3 and the compound of Formula 2 obtained as described above is a mixture including the compound of Formula 1a and the compound of Formula 1b:

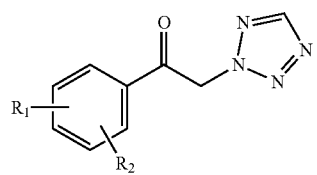

[Formula 1a]

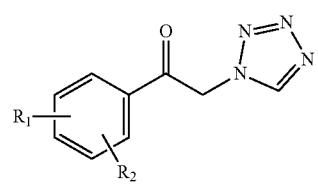

[Formula 1b]

wherein $R_1$ and $R_2$ are the same as defined above.

Therefore, in order to separate the compound of Formula 1a and the compound of Formula 1b from each other in the reaction product, the method for preparing the compound of Formula 1a may further include purifying the reaction product of the salt of the compound of Formula 3 and the compound of Formula 2.

In one embodiment, the purifying step may include a crystallization process, and more particularly, the crystallization process may include a first crystallization process and a second crystallization process.

In one embodiment, the crystallization process may be a process in which a first crystallization solvent (for example, water, $C_1$-$C_4$ lower alcohol, diethyl ether, tert-butyl methyl ether, isopropyl ether, pentane, hexane, cyclohexane, heptane and a mixture thereof) is added to a reaction product of a salt of a compound of Formula 3 and a compound of Formula 2, the compound of Formula 1b is crystallized, and then filtered and separated ("first crystallization process"), a second crystallization solvent (for example, acetone, acetonitrile, tetrahydrofuran, 2-methyl tetrahydrofuran, ethyl acetate, isopropyl acetate, n-butyl acetate, dichloromethane, chloroform, 1,4-dioxane, $C_1$-$C_4$ lower alcohol or a mixture thereof) is added to the remaining filtrate, and the compound of Formula 1a is crystallized, filtered and separated ("second crystallization process").

In one embodiment, a process of washing and concentrating may be further carried out before the first crystallization solvent is added, if necessary.

In one embodiment, the purifying step may include a heat treatment process. Through a heat treatment process, the compound of Formula 1b may be transformed to the compound of Formula 5.

In one embodiment, the heat treatment process may be carried out at a pressure of about 1 atmosphere to 50 atmosphere. The pressure is measured for internal pressure of the reactant and the pressure may depend on the change of the temperature in the reactant.

In one embodiment, the heat treatment process may be carried out at a reaction temperature of 100° C. to 250° C., preferably 150° C. to 220° C.

In one embodiment, the heat treatment process may be carried out for 10 minutes to 40 hours, preferably 20 minutes to 24 hours. However, the reaction time may be appropriately adjusted according to the reaction temperature.

In one embodiment, the heat treatment process may be a step of heating the reaction product of the salt of the compound of Formula 3 and the compound of Formula 2 to selectively convert only the compound of Formula 1b into the compound of Formula 5 (wherein because the compound of Formula 1a is thermally stable compared to the compound of Formula 1b, the ratio of decomposition or reaction of the compound of Formula 1a due to the heat treatment is extremely low compared to the compound of Formula 1b). The heating may be carried out in the presence of a solvent (e.g., acetone, acetonitrile, tetrahydrofuran, 2-methyl tetrahydrofuran, ethyl acetate, isopropyl acetate, n-butyl acetate, dichloromethane, chloroform, 1,4-dioxane, $C_1$-$C_4$ lower alcohol or a mixture thereof).

After the heat treatment process, a process of washing with an acidic aqueous solution may be further carried out. Through a process of washing, the compound of Formula 5, which is transformed from the compound of Formula 1b, is removed.

In one embodiment, the acidic aqueous solution may be a solution of strong acid such as hydrochloric acid or sulfuric acid, or a solution of weak acid such as acetic acid or citric acid, but is not limited thereto.

[Formula 5]

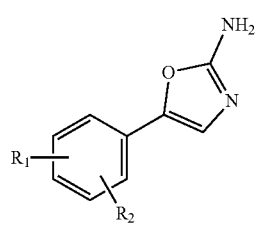

wherein $R_1$ and $R_2$ are the same as defined above.

According to the present disclosure, when the compound of Formula 3 is prepared as a salt and then reacted with the compound of Formula 2, the compound of Formula 1a can be obtained with increased selectivity as compared to a conventional method in which the compound of Formula 2, the compound of Formula 3 and the base are simultaneously reacted. Specifically, the ratio of the compound of Formula 1a to the compound of Formula 1b was 4:6 in the conventional method, but the ratio may become about 6:4 according to the method of the present disclosure.

As the selectivity of the compound of Formula 1a is increased according to the method of the present disclosure compared to the conventional method as described above, the productivities of the compound of Formula 1a and carbamate compound prepared therefrom may also increase remarkably. Specifically, their productivities increase at least about 70%, and more specifically, about 70% to about 100%.

Therefore, another aspect of the present disclosure relates to a method for increasing the selectivity of a compound of Formula 1a by using a salt of a compound of Formula 3 in the synthesis of compounds of Formula 1a and a compound of Formula 1b from a compound of Formula 2 and a compound of Formula 3.

In addition, still another aspect of the present disclosure relates to a preparing a compound of Formula 1a, comprising: reacting a compound of Formula 2 with a salt of a compound of Formula 3; and purifying the reaction product of the salt of the compound of Formula 3 and the compound of Formula 2, wherein the purifying step comprises a crystallizing process or a heat treatment process:

[Formula 1a]

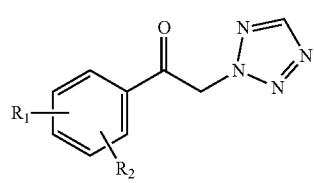

[Formula 2]

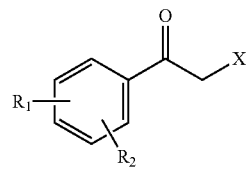

[Formula 3]

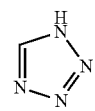

wherein $R_1$, $R_2$ and X are the same as defined above.

In addition, still another aspect of the present disclosure relates to a method for preparing a compound of Formula 4, comprising: (1) reacting a compound of Formula 2 with a salt of a compound of Formula 3; (2) separating the compound of Formula 1a from a mixture obtained from the reaction of step (1); and (3) reducing the compound of Formula 1a separated in step 2 and carbamating the reduced compound of Formula 1a:

[Formula 4]

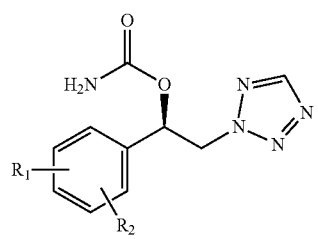

wherein $R_1$ and $R_2$ are the same as defined above.

The reaction of a compound of Formula 2 and a compound of Formula 3 is the same as described above.

The separation of a compound of Formula 1a may include the purification step described above.

In the step of reducing and carbamating, the reduction process may be carried out by using an oxidoreductase enzyme that is suspended in a reaction mixture or immobilized in a conventional manner. The enzyme may be used in a completely purified state, a partially purified state or a microbial cell state in which it is expressed. The cells themselves may be in a native state, permeabilized state, or lysed state. It will be understood by those of ordinary skill in the art that when the method of the present disclosure is carried out by the use of enzyme in a cell state allows to highly reduce costs so that it is preferable. Most preferably, the enzyme is expressed in *E. coli* and used as a native cell suspension.

The enzymatic reduction of the compound of Formula 1a may be carried out in a reaction mixture comprising the compound of Formula 1a, an oxidoreductase, NADH or NADPH as a cofactor, a cosubstrate and a suitable buffer. The oxidoreductase can be used to reduce the compound of Formula 1a with high conversion and enantiomeric selectivity using polypeptides having oxidoreductase activity. The enantiomeric excess of the R-configuration alcohol produced in the enantiomeric selective enzymatic reduction is at least about 89%, preferably at least about 95% and most preferably at least about 99%.

In the step of reducing and carbamating, a method for introducing a carbamoyl group may, for example, introduce a carbamoyl group by the use of an inorganic cyanate-organic acid, isocyanate-water or a carbonyl compound-ammonia.

In the carbamation with the inorganic cyanate-organic acid, the (R)-configuration alcohol compound converted from the compound of Formula 1a by the reduction method may be dissolved in an organic solvent—for example, diethylether, tetrahydrofuran, 1,4-dioxane, acetonitrile, dichloromethane, chloroform or a mixture thereof, and then an inorganic cyanate such as sodium cyanate and an organic acid such as methanesulfonic acid or acetic acid, which are 1 to 4 equivalents, may be added thereto, and the reaction may be carried out at a reaction temperature of about −10° C. to about 70° C.

In the method of using isocyanate-water, 1 to 4 equivalents of isocyanate—for example, chlorosulfonyl isocyanate, trichloroacetyl isocyanate, trimethylsilyl isocyanate or the like, may be added to an alcohol compound solution having a (R)-configuration by reducing a compound of Formula 1a in an organic solvent—for example, diethylether, tetrahydrofuran, 1,4-dioxane, acetonitrile, dichloromethane, chloroform or a mixture thereof, and reacted at a reaction temperature of about −50° C. to 40° C., and then 1 to 20 equivalents of water may be sequentially added thereto without any purification to carry out hydrolysis.

In the method of using carbonyl compound-ammonia, 1 to 4 equivalents of carbonyl compound—for example, 1,1'-carbonyldiimidazole, carbamoyl chloride, N,N'-disuccinimidyl carbonate, phosgene, triphosgene, chloroformate or the like, are added to an alcohol compound solution in a (R)-configuration obtained by reducing a compound of Formula 1a in an organic solvent—for example, diethylether, tetrahydrofuran, 1,4-dioxane, acetonitrile, dichloromethane, chloroform or a mixture thereof, and then 1 to 10 equivalents of ammonia are sequentially added without purification at a reaction temperature of about −10° C. to 70° C.

In addition, still another aspect of the present disclosure relates to a method for separating a compound of Formula 1a from a mixture comprising a compound of Formula 1a and a compound of 1b by heat treating the mixture comprising the compound of chemical formula 1a and the compound of Formula 1b to produce a compound of Formula 5 and removing this compound.

The heat treatment process is the same as described above.

In one embodiment, the removal of the compound of Formula 5 may be carried out by washing with an acidic aqueous solution. The acidic aqueous solution may be a solution of strong acid such as hydrochloric acid or sulfuric acid, or a solution of weak acid such as acetic acid or citric acid, but is not limited thereto.

Hereinafter, the present invention will be specifically described with reference to the following examples. However, these are provided only for better understanding of the present invention, and the scope of the present invention is not limited thereto.

EXAMPLES

Example 1

Tetrazole (0.165 g) was dissolved in methanol (9 mL) and potassium carbonate (0.538 g) was added thereto at room temperature. The reaction product was stirred at room temperature for about 15 minutes. After confirming that carbon dioxide gas no longer occurs, n-butyl acetate (9 mL) was added, methanol was removed by distillation under reduced pressure, and n-butyl acetate was added. After adding 2-bromo-2'-chloroacetophenone (0.50 g) to the reaction solution, the reaction product was stirred at 50° C. for 12 hours. After the temperature was adjusted to room temperature, it was confirmed that the selectivity of the compound of Formula 1b corresponding to Formula 1b was 40% and the selectivity of the compound of Formula 1a corresponding to Formula 1a was 60%, by HPLC. The HPLC conditions are as follows and are as used in the examples below:

The column was Phenomenex Luna C18, 5 µm, 4.6×250 mm and column temperature was 35° C. The mobile phase was acetonitrile:water at a ratio of 6:4 and contained 0.1% trifluoroacetic acid, and was flowed for 10 minutes at 2.0 mL/min under isocratic conditions. The wavelength was fixed at 245 nm, and the peak time position of the compound was 2.36 minutes for the compound of Formula 1a, 1.94 minutes for the compound of Formula 1b, and 4.01 minutes for 2-bromo-2'-chloroacetophenone.

HPLC results are represented in FIG. 1.

Example 2

Tetrazole (0.165 g) was dissolved in n-butyl acetate (9 mL) and potassium carbonate (0.538 g) was added at room temperature. The reaction product was stirred at room temperature for about 24 hours. After confirming that carbon dioxide gas no longer occurred, 2-bromo-2'-chloroacetophenone (0.50 g) was added to the reaction solution and the reaction product was stirred at 50° C. for 12 hours. After the temperature was adjusted to room temperature, it was confirmed that the selectivity of the compound of Formula 1a was 60% by HPLC.

Example 3

Tetrazole (1.40 g) and potassium carbonate (1.38 g) were added to water (10 mL) and stirred at 100° C. for about 1 hour under a reflux condition. The temperature was lowered to room temperature, water was distilled off, and the resultant was diluted in 20 mL of ethanol. The mixture was stirred at 80° C. for 2 hours, and then the temperature was adjusted at room temperature. About 10 mL of ethanol was removed by distillation under reduced pressure and stirred for 2 hours, then filtered and dried under a nitrogen atmosphere to obtain the tetrazole potassium salt (1.70 g). The obtained tetrazole potassium salt (0.153 g) was added to n-butyl acetate (1.8 mL), 2-bromo-2'-chloroacetophenone (0.30 g) was added thereto, and the reaction mixture was stirred at 50° C. for 12 hours. After the temperature was adjusted to room temperature, it was confirmed that the selectivity of the compound of Formula 1a was 62% by HPLC.

Example 4

The tetrazole potassium salt (0.509 g) obtained in Example 3 was added to 2-methyl tetrahydrofuran (6 mL), 2-bromo-2'-chloroacetophenone (1.00 g) was added thereto, and the reaction mixture was stirred at 50° C. for 22 hours. After the temperature was adjusted to room temperature, it was confirmed that the selectivity of the compound of Formula 1a was 57% by HPLC.

Example 5

Tetrazole (1.40 g) and cesium carbonate (3.26 g) were added to water (10 mL) and stirred at 100° C. for about 1 hour under a reflux condition. The temperature was lowered to room temperature, water was distilled off, and the reaction mixture was vacuum-dried to obtain tetrazole cesium salt (1.685 g). The obtained tetrazole cesium salt (0.285 g) was added to n-butyl acetate (1.8 mL), 2-bromo-2'-chloroacetophenone (0.30 g) was added thereto, and the reaction mixture was stirred at 50° C. for 12 hours. After the temperature was adjusted to room temperature, it was confirmed that the selectivity of the compound of Formula 1a was 56% by HPLC.

Example 6

Tetrazole (1.40 g) and sodium carbonate (0.68 g) were added to water (10 mL) and stirred at 100° C. for about 1 hour under a reflux condition. The temperature was lowered to room temperature, water was distilled off, and the reaction mixture was vacuum-dried to obtain tetrazole sodium salt (1.53 g). The obtained tetrazole sodium salt (0.156 g) was added to n-butyl acetate (1.8 mL), 2-bromo-2'-chloroacetophenone (0.30 g) was added thereto, and the reaction mixture was stirred at 50° C. for 12 hours. After the temperature was adjusted to room temperature, it was confirmed that the selectivity of the compound of Formula 1a was 63% by HPLC.

Comparative Example 1

2-Bromo-2'-chloroacetophenone (86.0 g), potassium carbonate (30.5 g) and 35% tetrazole DMF solution (81.0 g) were added to ethyl acetate (245 mL) and stirred at 55° C. for 2 hours. After the temperature was adjusted to room temperature, it was confirmed that the selectivity of the compound of Formula 1a was 42% by HPLC.

Example 7

2-Bromo-2'-chloroacetophenone (13.0 g) was reacted with tetrazole potassium salt (6.62 g) and isopropyl acetate (117 mL), and then washed with diluted hydrochloric acid and brine to remove secondarily generated potassium bromide. The separated isopropyl acetate layer was completely concentrated, substituted with tert-butyl methyl ether, stirred under a reflux condition for about 1 hour, and then slowly cooled to 15° C. When the compound of Formula 1b was sufficiently precipitated, the resultant was filtered to obtain the compound of Formula 1b (4.1 g, including the compound of Formula 1a) as a solid. For reference, the filtrate was analyzed by HPLC, and it was confirmed that the filtrate is comprised of 6.0 g of the compound of Formula 1a and 0.74 g of the compound of Formula 1b.

Compounds of Formula 1b: 1H NMR (CDCl$_3$) 8.86 (s, 1H), 7.77 (d, 1H), 7.40-7.62 (m, 3H), 5.97 (s, 2H)

Example 8

A solution of a mixture of 6.0 g of the compound of Formula 1a and 0.74 g of the compound of Formula 1b obtained as a filtrate in Example 7 was concentrated under reduced pressure to remove the solvent as much as possible, and while being substituted with isopropyl alcohol, the compound of Formula 1a was dissolved in isopropyl alcohol (45 mL), stirred for about 1 hour at 60° C., and slowly cooled to 10° C. The compound of Formula 1a was filtered after sufficient precipitation, washed twice with cooled isopropyl alcohol (13 mL) and once with n-heptane (26 mL) to obtain the compound of Formula 1a (5.55 g) as a solid with an HPLC purity of 94.2%.

Compounds of Formula 1a: 1HNMR (CDCl$_3$) 8.62 (s, 1H), 7.72 (d, 1H), 7.35-7.55 (m, 3H), 6.17 (s, 2H)

Example 9

After reacting 2-bromo-2'-chloroacetophenone (17.1 g) with tetrazole potassium salt (8.71 g) and isopropyl acetate (130 mL), heptane (165 mL) was added to obtain the secondarily produced potassium bromide and the compound of Formula 1b as a solid at one time. After stirring at 60° C. for 1 hour, the reaction mixture was slowly cooled to about 8.5° C. When the potassium bromide and the compound of Formula 1b were sufficiently precipitated, they were filtered to obtain potassium bromide and the compound of Formula 1b (total of 14 g) as solids. For reference, the filtrate was analyzed by HPLC, and it was confirmed that the filtrate is comprised of 9.5 g of the compound of Formula 1a and 1.4 g of the compound of Formula 1b.

Example 10

A solution of a mixture of 9.5 g of the compound of Formula 1a and 1.4 g of the compound of Formula 1b—obtained as a filtrate in Example 9—was concentrated under reduced pressure to remove the solvent as much as possible and substituted with isopropyl alcohol. The compound of Formula 1a was stirred for about 1 hour at 60° C. to dissolve in isopropyl alcohol (96 mL) and then slowly cooled to 10° C. When the compound of Formula 1a was sufficiently precipitated, the solid was filtered and washed twice with cold isopropyl alcohol (17 mL) and once with heptane (34 mL). The compound of Formula 1a (7.6 g) was obtained as a solid.

Example 11

A mixture in which 2'-chlorophenyl 2-tetrazol-2-yl ketone (0.3 g) and 2'-chlorophenyl 2-tetrazole-1-yl ketone (0.2 g) were dissolved in isopropyl acetate (3 mL) was heated at 150° C. for 24 hours, the temperature was adjusted to room temperature, and a pyrolysis ratio was confirmed through HPLC. It was confirmed that 99.9% of 2'-chlorophenyl 2-tetrazol-1-yl was decomposed and transformed to 5-(2-chlorophenyl)oxazol-2-amine, and 88.2% of 2'-chlorophenyl 2-tetrazol-2-yl remained without decomposition by HPLC. The produced 5-(2-chlorophenyl)oxazol-2-amine was washed with 1N HCl to remove this compound.

5-(2-Chlorophenyl)oxazol-2-amine: LC-MS [M+H] =195.0 g/mol

Figure 2:
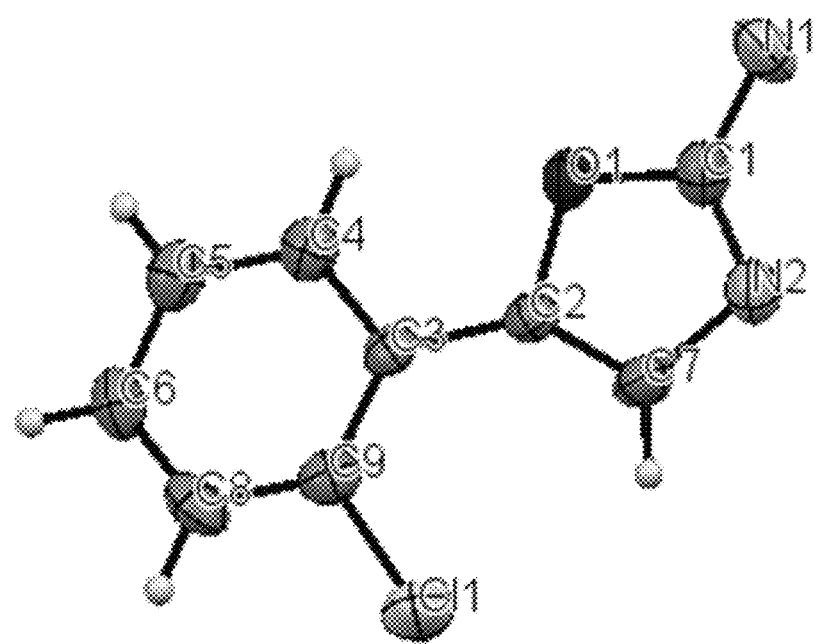
FIG. 2 is an ORTEP (Oak Ridge Thermal Ellipsoid Plot) image of the structure of 5-(2-chlorophenyl)oxazol-2-amine obtained in Example 10.

The structure of 5-(2-chlorophenyl)oxazol-2-amine was confirmed by ORTEP image and represented in FIG. 2.

Example 12

A mixture in which 2'-chlorophenyl 2-tetrazol-2-yl ketone (0.3 g) and 2'-chlorophenyl 2-tetrazole-1-yl ketone (0.2 g) were dissolved in isopropanol (3 mL) was flowed in a tube-type continuous reactor set at 210° C. for 20 minutes, and then the temperature was adjusted to room temperature, and a pyrolysis ratio was confirmed through HPLC. It was confirmed that 99.9% of 2'-chlorophenyl 2-tetrazol-1-yl was decomposed and transformed to 5-(2-chlorophenyl)oxazol-2-amine, and 90% of 2'-chlorophenyl 2-tetrazol-2-yl remained without decomposition.

What is claimed is:

1. A method for preparing a compound of Formula 1a, comprising:

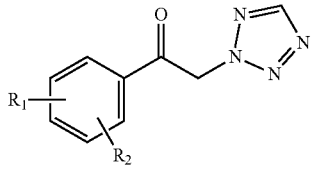

Formula 1a reacting a compound of Formula 2 with a salt of a compound of Formula 3; and purifying the reaction product of the salt of the compound of Formula 3 and the compound of Formula 2, wherein the purifying step comprises a crystallizing process or a heat treatment process;

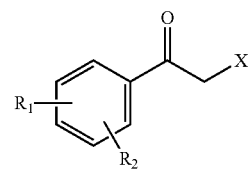

Formula 2

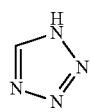

Formula 3 wherein $R_1$ and $R_2$ are each independently selected from the group consisting of hydrogen, halogen, perfluoroalkyl having 1 to 8 carbon atoms, alkyl having 1 to 8 carbon atoms, thioalkoxy having 1 to 8 carbon atoms, and alkoxy having 1 to 8 carbon atoms; and X is a leaving group.

2. The method according to claim 1, wherein the salt of the compound of Formula 3 is obtained by reacting the compound of Formula 3 with a base.

3. The method according to claim 2, wherein the base is an inorganic base or an organic base.

4. The method according to claim 3, wherein the inorganic base is a metal hydroxide or a metal carbonate, and the organic base is an amine compound.

5. The method according to claim 4, wherein the metal hydroxide is selected from lithium hydroxide, sodium hydroxide and potassium hydroxide; the metal carbonate is selected from lithium carbonate, sodium carbonate, potassium carbonate and cesium carbonate; and the amine compound is selected from triethylamine and diisopropylethylamine.

6. The method according to claim 2, wherein the compound of Formula 3 is reacted with a base in a reaction solvent, and then the salt of the compound of Formula 3 separated from the reaction product is reacted with the compound of Formula 2.

7. The method according to claim 2, wherein after reacting the compound of Formula 3 with a base, the compound of Formula 2 is added to the reaction product to react with the salt of the compound of Formula 3.

8. The method according to claim 1, wherein the crystallizing process comprises a first crystallizing process and a second crystallizing process.

9. The method according to claim 8, wherein a solvent of the first crystallizing process is selected from the group consisting of water, $C_1$-$C_4$ lower alcohol, diethyl ether, tert-butyl methyl ether, isopropyl ether, pentane, hexane, cyclohexane, heptane and a mixture thereof.

10. The method according to claim 8, wherein a solvent of the second crystallizing process is selected from the group consisting of acetone, acetonitrile, tetrahydrofuran, 2-methyl tetrahydrofuran, ethyl acetate, isopropyl acetate, n-butyl acetate, dichloromethane, chloroform, 1,4-dioxane, $C_1$-$C_4$ lower alcohol and a mixture thereof.

11. The method according to claim 1, wherein the purifying step is a heat treatment process which comprises washing with an aqueous acidic solution.

12. The method according to claim 1, wherein the leaving group is selected from the group consisting of chloride, bromide, mesylate, tosylate and 4-nitrophenyl sulfonate.

* * * * *